(12) United States Patent
Schlaudraff

(10) Patent No.: US 9,335,534 B2
(45) Date of Patent: May 10, 2016

(54) SPECIMEN SLIDE HAVING REFERENCE POINTS

(71) Applicant: Leica Microsystems CMS GmbH, Wetzlar (DE)

(72) Inventor: Falk Schlaudraff, Butzbach/Nieder-Weisel (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 220 days.

(21) Appl. No.: 13/969,910

(22) Filed: Aug. 19, 2013

(65) Prior Publication Data

US 2014/0049818 A1 Feb. 20, 2014

(30) Foreign Application Priority Data

Aug. 17, 2012 (DE) .......................... 10 2012 214 664

(51) Int. Cl.
| | | |
|---|---|---|
| *G02B 21/34* | (2006.01) | |
| *G03F 7/20* | (2006.01) | |
| *G02B 21/36* | (2006.01) | |

(52) U.S. Cl.
CPC ................ *G02B 21/34* (2013.01); *G02B 21/36* (2013.01); *G03F 7/20* (2013.01)

(58) Field of Classification Search
CPC ...................... G02B 21/34; B01J 2219/00542; G01N 2001/282
USPC ................ 359/357, 396; 356/244; 435/288.3, 435/288.7; 436/46; 206/456
See application file for complete search history.

(56) References Cited

U.S. PATENT DOCUMENTS 4,183,614 A * 1/1980 Feldman ................ G02B 21/34
                                                        359/397
2009/0291195 A1* 11/2009 Angros ........................ 427/2.11

FOREIGN PATENT DOCUMENTS

| DE | 10100246 A1 | 7/2002 |
|---|---|---|
| DE | 10336803 A1 | 3/2005 |
| DE | 102005036529 A1 | 2/2007 |
| JP | 2009036969 A | 2/2009 |
| WO | 9828592 A1 | 7/1998 |
| WO | 03036266 A1 | 5/2003 |

OTHER PUBLICATIONS

Mulisch, M. And Welsch, U. (eds.): ROMEIS—Mikroskopische Technik [Microscopy technique], 2010, 10th ed., Heidelberg: Spektrum Akademischer Verlag.

* cited by examiner

*Primary Examiner* — Bumsuk Won
*Assistant Examiner* — Grant Gagnon
(74) *Attorney, Agent, or Firm* — Patentbar International, P.C.

(57) ABSTRACT

A specimen slide (100) having a sample region (101) in which a sample (200) that can be investigated microscopically can be arranged, and that comprises reference points (A-Z, 1-24, a-j, α-κ) arranged at least in the sample region (101), is proposed. The reference points (A-Z, 1-24, a-j, α-κ) are embodied in such a way that on the basis of an identification of at least a stipulated number of reference points (A-Z, 1-24, a-j, α-κ) in an arbitrary sub-region (102) of the sample region (101), the position of the arbitrary sub-region (102), and/or at least one position therein, on the specimen slide (100) can be unequivocally determined A method for determining and/or retrieving a position on a corresponding specimen slide, and a corresponding sample investigation system, are likewise subjects of the invention.

12 Claims, 2 Drawing Sheets

SPECIMEN SLIDE HAVING REFERENCE POINTS

RELATED APPLICATIONS

This application claims priority to German Patent Application No. DE 10 2012 214 664.4, filed Aug. 17, 2012, which is incorporated herein by reference in its entirety.

FIELD OF THE INVENTION

The present invention relates to a specimen slide having reference points, to a method for determining and/or retrieving a position on such a specimen slide, and to a corresponding sample investigation system.

BACKGROUND OF THE INVENTION

Only in the rarest cases are microscopic samples investigated directly and without further processing in a light microscope or even an electron microscope. Most microscopy inquiries and specimens require more or less comprehensive preparation.

Material to be examined microscopically is usually fixed and embedded. Sample sections can be produced from the embedded material, for example using a microtome. These can be stained and, after placement onto a specimen slide, visually investigated and/or digitized. An overview of corresponding techniques is provided, for example, by Mulisch, M. and Welsch, U. (eds.): Romeis-Mikroskopische Technik [Microscopy technique], 10th ed., Heidelberg: Spektrum Akademischer Verlag, 2010.

Microscopes are generally used to detect small structures not detectable with the naked eye, and to locate characteristic features in such structures. A basic microscopy task in cytology, histology, and pathology is to scan a prepared specimen and examine it for structures, cells, cell groups, and the like that are of interest. Once the locations of such structures on the prepared specimen have been found, it is desirable for many reasons to remember them. For example, a structure must be located again at a later point in time by the same or another user for purposes of checking or further inspection, or for quality assurance reasons.

Many microscopes have for this purpose a unit for ascertaining the coordinates of positions of a point in a device-dependent coordinate system. The position that has been located can be traveled to later by ascertaining those coordinates electromechanically The coordinates are conventionally device-dependent, i.e. the coordinates can be exactly reproduced for that device only if no changes have been made in microscope alignment and if no tolerances exist. If, however, the microscope stage has been removed for repair and reattached, for example, it may possibly furnish for the same location on the prepared specimen coordinates different from those originally determined The coordinate systems of different microscopes, even those of the same model or the same series, are also not (exactly) identical.

This is even more relevant if the corresponding coordinates are to be reproduced not in a microscope but in a sample processing device such as, for example, a (laser) microdissection unit, or if the coordinates are determined not in a microscope but rather, for example, in a slide scanner. The more different the configuration of the respective devices involved, the more complex an interchange generally turns out to be.

DE 103 36 803 A1 discloses a method and a system for device-independent determination of coordinates of a point imaged by means of a microscope. Provision is made here that firstly, for predetermined specimen-related reference coordinates of at least one reference point in a DICOM (Digital Imaging and COmmunications in Medicine) coordinate system, the associated device coordinates of the at least one imaged reference point are determined in a device-dependent coordinate system, and a transformation rule for converting device-dependent coordinates into the coordinates of the DICOM coordinate system is identified. The device coordinates of the imaged point can then be converted, by means of the transformation rule that has been discovered, into device-independent coordinates of the DICOM coordinate system.

This method and system prove to be complex in practice, however, since all the devices involved must each be set up to carry out the necessary steps and must possess corresponding calculation units, e.g. for ascertaining the transformation rule.

A need therefore continues to exist for, in particular, simplified capabilities for determining and/or retrieving a position on a specimen slide, in particular in a sample investigation system made up of the different components explained above.

SUMMARY OF THE INVENTION

In light of this, the present invention proposes a specimen slide having reference points, a method for determining and/or retrieving a position on such a specimen slide, and a corresponding sample investigation system, having the features of the independent claims. Preferred embodiments are the subject matter of the dependent claims and of the description that follows.

ADVANTAGES OF THE INVENTION

The present invention proposes a specimen slide on which a microscopically viewable sample can be arranged in a sample region, and which comprises reference points at least in the sample region. The reference points are embodied in such a way that on the basis of an identification of at least a stipulated number of reference points in an arbitrary sub-region (i.e. one freely selectable in terms of position within the sample region) of the sample region, the position of the arbitrary sub-region, and/or at least one position in that arbitrary sub-region, on the specimen slide can be unequivocally determined.

As also explained in more detail below, the arbitrary sub-region of the sample region is advantageously a respective region viewable in a field of view or evaluation field in a microscope or in another evaluation device. This of course depends on the viewing magnification, so that sub-regions of the sample region that are of different sizes can be viewed at different viewing magnifications.

According to the meaning of "arbitrary" used herein, these sub-regions of different sizes can each be selected freely within the sample region. This can be accomplished, for example, by displacement of the specimen slide by means of a cross-slide stage, so that sub-region becomes displaced relative to the sample region. A position determination is thereby possible, provided the respective corresponding sub-region comprises at least the stipulated number of reference points.

The present invention has the substantial advantage, as compared with the existing art, that an accurate determination and/or retrieval of a position can now be carried out in reliable and uncomplicated fashion based on an identification of corresponding reference points on the specimen slide itself, e.g. by pattern recognition. In the simplest case, namely when reference points that can be sensed visually are provided, a single glance through a microscope is sufficient to unequivocally localize a corresponding sub-region or corresponding positions therein. This is also true correspondingly for automatic sensing or identification. In particular, the marks that are respectively present no longer need to be laboriously incorporated or converted into a device-dependent or device-independent coordinate system. The specimen slide itself already possesses all the means for performing an accurate position determination.

The position to be determined and/or retrieved is, for example, that of a sample region that either is to be further investigated microscopically, for example after corresponding staining, or is to be subjected to a sample processing method. The method is suitable in particular for sample processing by laser microdissection.

The invention also makes possible simple and reliable transfer of corresponding position data, for example from a microscope system or a slide scanner, to a sample processing device. For this, the sample can be sensed, for example, visually by a human viewer or automatically, for example by a corresponding evaluation system. Reference points identified in the context of this sensing can be noted and/or stored. The identified reference points can be used to define a single point but also, for example, to define an area. An individual point can, for example, coincide with a reference point and/or can be defined by a crosshairs that is determined by multiple reference points. An area can be larger or smaller than the sub-region and can be defined, for example, by a polygon laid out between multiple reference points. It is thereby defined by multiple positions in the arbitrary sub-region. Those positions in turn can be unequivocally spatially determined based on the embodiment according to the present invention of the reference points on the specimen slide.

The respectively relevant reference points, as well as a linkage instruction if applicable (e.g. "crosshairs between reference points" or "polygon"), can be communicated to the sample processing device. This can be accomplished, for example, by manual input and/or by means of cable-based or wireless communication systems. The sample processing device is then in turn advantageously set up to derive a processing instruction from the respectively relevant reference points and, if applicable, from the linkage instruction. For example, a sample processing device embodied as a laser microdissection unit can be set up to eject a structure, cells, or cell groups of interest at the intersection point of a crosshairs, and/or to cut out a sample region that is defined by a polygon, by means of a laser beam.

The aforesaid actions can be supplemented or replaced by manual and/or virtual mark. For example, a human observer can make a mark using known input means, for example a computer mouse and/or capacitive displays (touchscreens), on an image of a sub-region of a specimen slide created by a sample sensing device, for example a slide scanner and/or a video microscope. In the case of touchscreens, this can also be accomplished, for example, using corresponding gestures. This mark has a relationship to reference points on the specimen slide in the sub-region that have been identified by means of the slide scanner and/or video microscope. The sample sensing device can create a spatial relationship between the marks made by the human observer and the reference points. This spatial relationship, and/or an associated linkage instruction specified as applicable by the human observer (for example, as above, "crosshairs" or "polygon"), can then be outputted by the sample sensing device and/or transferred to a sample processing device.

Here as well, the spatial relationship and/or the reference points and/or the associated linkage instruction, also referred to in the context of this Application as "reference point data," are converted into a processing instruction, and the sample is processed in accordance with the processing instruction as explained above.

The actions according to the present invention make it possible, for example, to implement an integrated sample investigation system for oncological inquiries. This system encompasses, for example, a slide scanner with which a sample, for example a patient's tissue, can be scanned for specific features, for example tumor cells. On positive sections, for example tumor-positive sections, the position of the tumor tissue can be determined exactly. Data regarding the position of the tumor tissue, and optionally data regarding a desired type of processing, can be transferred to a corresponding sample processing unit, for example a laser microdissection unit. Tumor tissue that is to be subjected to a biochemical investigation or the like can be cut out selectively and with high spatial precision using the laser microdissection unit, and transferred into corresponding sample vessels.

In contrast to the constant (re)calibration of corresponding systems that is conventionally necessary, which must occur on all devices involved, is tolerant to only a small extent, and is moreover susceptible to operating errors, the present invention makes possible an exact and largely calibration-independent position determination.

The simple transfer of position data between different devices that is possible thanks to a specimen slide according to the present invention allows investigation and sample processing to be significantly speeded up. Data regarding the respective marks can also be stored, for example, in the software of a sample sensing device and/or sample processing device, for example a laser microdissection unit, so that it can easily be retrieved. In addition, different reference point data corresponding to differently embodied reference points on the specimen slide can also be stored depending on the problem being addressed.

The specimen slides, marked with reference points and optionally coded, contain different reference points advantageously for different, but for at least one, magnification level, that are moreover unique for all X and Y coordinates in the field of view of a magnification level on the specimen slide. This makes it possible, for example, to localize plotted marks and/or sample regions relative to reference points that can respectively be sensed concurrently in a field of view. It is no longer necessary to refer to one or more reference points arranged outside the field of view, for example zero points of a coordinate system. As a result, now not only is it possible to determine the relative location of a specimen point with regard to a reference point, but the respective reference point or points itself or themselves indicate(s) a position of a sample. The more reference points that are used in this context, and the closer they are located to the marks to be transferred, the more accurately a corresponding sub-region can be defined.

Advantageously, the reference points are therefore provided in the form of at least two reference point networks (having reference points on the "nodes" of a network) that differ from one another at least in terms of a spacing of their reference points. This corresponds to the provision, as explained, of separate markings that can each be sensed at one magnification level of a sample investigation device.

In order to cover the usual magnification range of a microscope and/or slide scanner, more generally of a sample investigation device, the spacing of the reference points of at least one reference point network is equal to at least two, ten, or a hundred times the spacing of the reference points of at least one further reference point network. Any number of corresponding reference point networks can be provided in order to cover all usual magnification levels. This makes it possible, for example, firstly to roughly delimit a sample region of interest at low magnification. A precise position determination can be then be performed using a higher magnification.

A corresponding specimen slide thus comprises at least two reference point networks, the spacing of the reference points in the at least two reference point networks being respectively embodied so that for a stipulated viewing magnification and/or for a corresponding range of view magnifications, at least the stipulated number of reference points of the respective reference point network can respectively be identified simultaneously in a field of view of a microscope or of another sample investigation device. It is thus possible, as mentioned, to perform an exact position determination in each case, for example, by means of a single glance through a microscope. A reference to external reference points is no longer necessary, although it is still possible.

Depending on the embodiment of the reference points, the stipulated number that is used for position determination is one, two, or three. If a corresponding reference point system is used in which a sufficient number of different reference points (i.e. each defined unequivocally in terms of a position) is provided, sensing of a single reference point can be sufficient. For a comparatively low magnification, for example, reference points on a specimen slide can be sequentially numbered numerically or alphanumerically, so that an unequivocal position can also be determined on the basis of only one reference point. An example of the use of three reference points is depicted in the Figures below.

The reference points can be embodied as reference points that can be sensed optically and/or electromagnetically, for example as reference points that can be sensed magnetically and/or capacitively. This makes possible, as required, particularly simple identification by a human viewer on the one hand and/or by an automatic sample investigation device and/or sample processing device.

As already mentioned, the reference points can be embodied at least in part as alphanumeric reference points. This makes possible simple evaluation and position determination by a human viewer. In other cases it may also prove advantageous to embody the reference points at least in part machine-readably, for example in the form of two-dimensional barcodes, thereby enabling fully automatic position determination and/or retrieval. This can be advantageous, for example, in an automated sample investigation system, for example having a slide scanner and a laser microdissection unit.

In certain cases it can also prove to be advantageous to embody the reference points so they can be optically and/or electromagnetically sensed only under defined sensing or viewing conditions. For example, fluorescent reference points that are visible only under corresponding excitation light can be provided. This makes possible visual viewing, scanning, and/or documentation of a sample without interference by the reference points under the viewing, scanning, and/or documentation conditions (e.g. in white light). Position determination and/or retrieval can then occur under special detection light, for example UV light, in which the reference points can be sensed. Also a possibility is, for example, the use of bandpass filters that furnish a viewing, scanning, and/or documentation light not having a defined wavelength region of a detection light used for identification of the reference points.

As already explained in part, a method for determining and/or retrieving a position on a specimen slide is also provided according to the present invention. In this context, on the basis of an identification of at least a stipulated number of reference points in an arbitrary sub-region of the sample region, the position of the arbitrary sub-region on the specimen slide is unequivocally determined Reference can be made to the explanations above regarding the features and advantages of this method and of the sample investigation system described below.

A corresponding sample investigation system comprises at least one sample investigation device, in particular a microscope and/or a slide scanner, and a sample processing device, in particular a laser microdissection unit. The sample investigation device and the sample processing device are each set up to determine and/or retrieve a position on a specimen slide, as explained previously. A corresponding sample investigation system can therefore operate in partly or entirely automatic fashion as necessary.

Advantageously, the sample investigation device is set up to transfer reference point data to the sample processing device. The sample processing device is in turn set up to derive a processing instruction from the reference point data and to process a sample on the specimen slide in accordance with the processing instruction. Reference may likewise be made to the explanations above regarding the terms "reference point data" and "processing instructions" and the features understood thereby.

Further advantages and embodiments of the invention are evident from the description and the appended drawings. It is understood that the features recited above and those yet to be explained below are usable not only in the respective combination indicated, but also in other combinations or in isolation, without departing from the scope of the present invention.

The invention is schematically depicted in the drawings on the basis of an exemplifying embodiment and will be described in detail below with reference to the drawings.

DETAILED DESCRIPTION OF THE PREFERRED EMBODIMENTS

Figure 1:
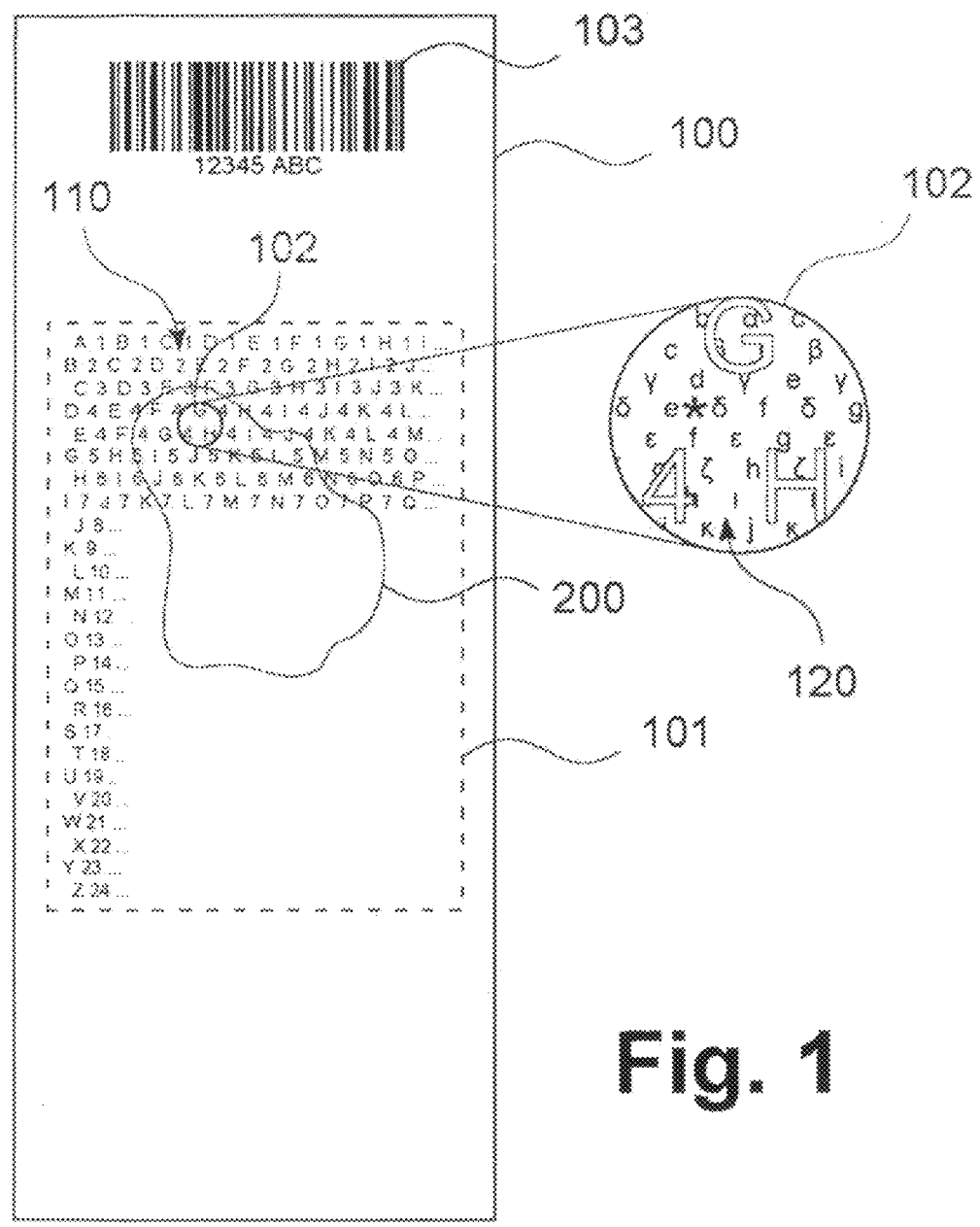
FIG. 1 schematically depicts a specimen slide having reference points, in accordance with a particularly preferred embodiment of the invention.

In the Figures, mutually corresponding elements are described using identical reference characters. Explanations are not repeated.

FIG. 1 schematically depicts a specimen slide 100 in accordance with a particularly preferred embodiment of the invention. Specimen slide 100 comprises a specimen region 101 on which a microscopically viewable specimen 200 can be arranged.

Depicted in sample region 101 are two reference point networks 110 and 120 that respectively comprise reference points A-Z, 1-24, a-j, and α-κ. An arbitrary subregion 102 in sample region 101 can be viewed, for example, using a microscope. Sub-region 102 is depicted in the left part of the Figure at original size and in the right part of FIG. 1 in magnified form. Reference point network 120 having reference points a-j and α-κ is visible only in the magnified depiction in the right part of the Figure.

The specimen slide can also comprise, for example, further identification features such as a barcode 103, which can be provided e.g. in order to associate a sample 200 with a patient.

As is apparent from FIG. 1, sub-region 102 of sample region 101 can be unequivocally identified by the reference points G, 4, and H of reference point network 110. These are present, in the triple combination depicted, only at a single position of specimen slide 100 or of its sample region 101. This makes possible an unequivocal position determination. As explained, reference points A-Z, 1-24, a-j, α-κ can also be embodied in such a way that they are visible only under specific viewing conditions, for example under UV light or light of a specific wavelength.

The entire sub-region 102 is thus unequivocally localized on specimen slide 100. In the embodiment of FIG. 1 depicted, reference points A-Z and 1-24 are associated with a magnification level of low magnification. When a corresponding arbitrary sub-region has been localized by means of this reference point network 110, a higher-resolution position determination can be accomplished by means of reference point network 120 at higher magnification, as depicted in the right part of FIG. 1. A sample region marked with an asterisk, or a corresponding mark made by a viewer, can in turn be unequivocally localized in reference point network 120 by way of reference points d, e, and δ.

The sample region marked with the asterisk, or the corresponding mark made by a viewer, is thus localized in the entirety of sample region 101 unequivocally in reference point network 110 via reference points G, 4, and H, and in reference point network 120 via reference points d, e, and δ. The respectively higher-resolution reference points of a reference point network 120 can of course repeat within a respectively lower-resolution reference point network 110, provided an unequivocal identification is possible by way of the two reference point networks 110 and 120.

Although an alphanumeric reference point system is depicted in FIG. 1, in specific applications other reference point systems, in particular machine-readable reference point systems, can also be used. Reference points that can be selectably sensed optically and/or electromagnetically can also be used.

Correspondingly, a reference point system does not necessarily require three reference points for unequivocal localization. If suitable reference points are used, for example sequential numbers, two or only one reference point can also be sufficient for position determination.

Figure 2:
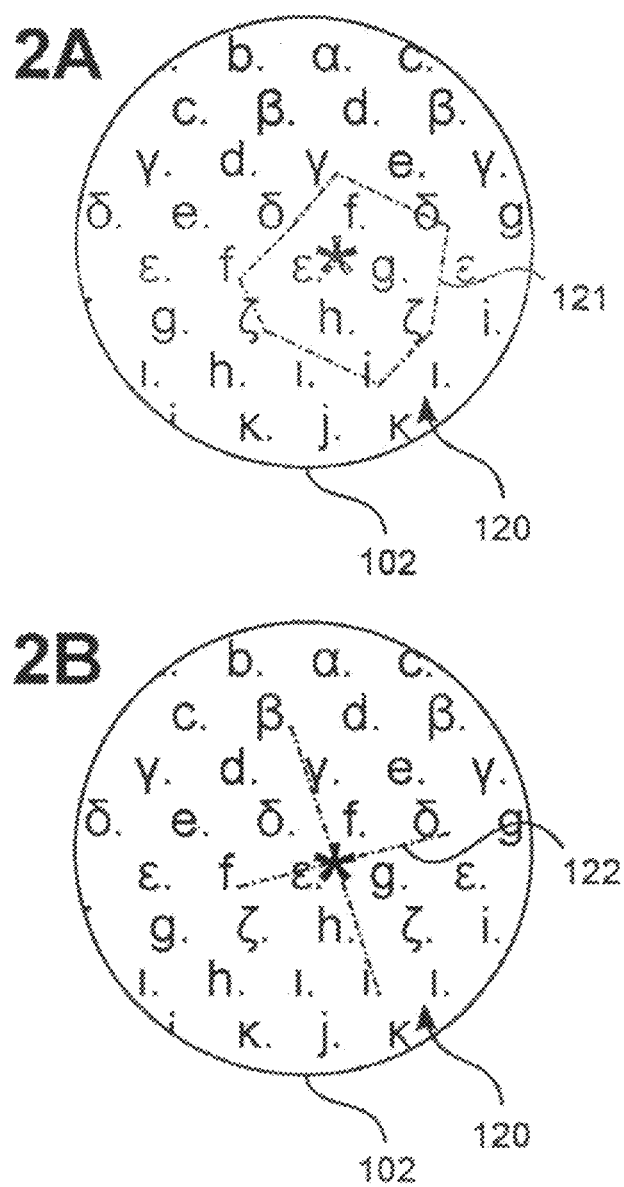
FIG. 2 shown as sub-figures 2A and 2B schematically depicts a sub-region of a sample region on a specimen slide having reference points, in accordance with FIG. 1.

FIG. 2 shows, in sub-figures 2A and 2B, possibilities for defining sample regions or positions within a sub-region 102. Sub-region 102 corresponds, for example, to the one of FIG. 1, although reference points G, 4, and H of reference point network 110 are omitted, and reference points a to j and α to κ of reference point network 120 are depicted, for the sake of clarity, with additional points.

Sub-figure 2A depicts an area 121, surrounded by a dot-dash line, that is defined by a polygon drawn clockwise between reference points γ, δ, ζ, i, ζ, f, and δ. The respective reference points γ, δ, ζ, i, ζ, f, and δ are uniquovocally defined by the reference points surrounding them. For example, the reference point ζ incorporated into the polygon at the lower left is surrounded by the reference points f, ε, h, ι, and g (clockwise), while the reference point ζ incorporated into the polygon at the lower right is surrounded by the reference points g, ε, i, ι, i, and h (clockwise). As explained, corresponding reference point data can be transferred reciprocally between different devices of a sample investigation system. A point of interest or a corresponding mark, indicated by an asterisk, is located inside area 121.

Sub-figure 2B depicts a crosshairs 122, likewise indicated using a dot-dash line, that is defined by the reference points β and i, and f and δ. The position of reference points β and i, and f and δ is in turn unequivocally defined by the reference points surrounding them. A point of interest or a corresponding mark, indicated by an asterisk, is marked by crosshairs 122.

What is claimed is:

1. A specimen slide having a sample region for microscopically investigating a sample in the sample region, the sample region being characterized by a first set of reference points that are visible in the sample region using a first magnification on a microscope, and a second set of reference points that are visible in a sub-region of the sample region using a second magnification greater than the first magnification, wherein a selected sub-region of the sample region is identified by an unique subset of a plurality of the first set of reference points, a mark is applied at a location within the selected sub-region, and the location of the mark within the selected sub-region is identified by an unique subset of second set reference points proximate to the mark within the selected sub-region, said unique subset of second set reference points further identified by a stipulated number of the proximate second set reference points within the selected sub-region.

2. The specimen slide according to claim 1, wherein the stipulated number of second set reference points is one, two, or three.

3. The specimen slide according to claim 1, wherein both the first and second sets of reference points can be sensed optically and/or electromagnetically.

4. The specimen slide according to claim 1, wherein both the first and second sets of reference points are at least in part represented as alphanumeric characters.

5. The specimen slide according to claim 1, wherein both the first and second sets of reference points are at least in part represented in machine-readable form.

6. The specimen slide according to claim 1, wherein both the first and second sets of reference points can be optically sensed only under defined viewing conditions such as in a predetermined wavelength region of a viewing light.

7. The specimen slide according to claim 1, wherein the first set of reference points and the second set of reference points differ from one another in terms of spacing between reference points in each set.

8. The specimen slide according to claim 7, wherein a spacing of the first set of reference points is a multiple of a spacing of the second set of reference points.

9. The specimen slide according to claim 7, wherein a spacing of the reference points in each of the first and second sets of reference points is respectively embodied such that at least the stipulated number of second set reference points and corresponding first set reference points can respectively be identified simultaneously for a predetermined size of the selected sub-region of the sample region.

10. A method for determining a position of a mark on a specimen slide, the method comprising:
providing a specimen slide having a sample region for microscopically investigating a sample;
placing a sample in the sample region, the sample region being characterized by a first set of reference points that are visible in the sample region using a first magnification on a microscope, and a second set of reference points that are visible in the sample region using a second magnification greater than the first magnification;

identifying a sub-region of the sample region by an unique subset of a plurality of the first set of reference points, applying the mark at the position within the identified sub-region, and identifying the position of the mark by an unique subset of a second set of reference points proximate to the mark within the identified sub-region, said unique subset of second set reference points further identified as a stipulated number of the proximate second set reference points.

11. A sample investigation system comprising:

at least one sample investigation device in a form of a microscope and/or a slide scanner; and a sample processing device in a form of a laser microdissection unit, the sample investigation device and/or the sample processing device being configured to determine and/or retrieve the position of the mark on the specimen slide with the sample according to the method recited in claim 10.

12. The sample investigation system according to claim 11, wherein the sample investigation device is configured to transfer first and second set reference point data to the sample processing device, and wherein the sample processing device is configured to derive a processing instruction from the first and second set reference point data and to process the sample on the specimen slide in accordance with the processing instruction.

* * * * *